United States Patent [19]
Kong et al.

[11] Patent Number: 5,573,171
[45] Date of Patent: Nov. 12, 1996

[54] METHOD OF THIN FILM PATTERNING BY REFLOW

[75] Inventors: Alvin M. W. Kong, Los Angeles; Chan A. Tu, West Covina, both of Calif.

[73] Assignee: TRW Inc., Redondo Beach, Calif.

[21] Appl. No.: 389,367

[22] Filed: Feb. 16, 1995

[51] Int. Cl.⁶ .......................... H01L 21/50; H01L 21/52
[52] U.S. Cl. .................... 228/123.1; 228/124.6; 228/195; 228/254; 427/123
[58] Field of Search .......................... 228/123.1, 124.1, 228/124.6, 195, 208, 215, 248.1, 254; 427/123

[56] References Cited

U.S. PATENT DOCUMENTS

| | | | |
|---|---|---|---|
| Re. 29,737 | 8/1978 | Boflum | 228/248.1 |
| 3,997,963 | 12/1976 | Riseman | 437/182 |
| 4,545,610 | 10/1985 | Lakritz et al. | 228/180.22 |
| 4,616,403 | 10/1986 | Schulte et al. | 437/5 |
| 4,729,003 | 3/1988 | Schulte et al. | 257/292 |
| 4,821,946 | 4/1989 | Abe et al. | 228/248.1 |
| 4,930,001 | 5/1990 | Williams | 257/737 |
| 5,024,372 | 6/1991 | Altman et al. | 228/254 |
| 5,124,175 | 6/1992 | Miracky et al. | 427/98 |
| 5,194,137 | 3/1993 | Moore et al. | 205/125 |
| 5,209,390 | 5/1993 | Temple et al. | 228/180.22 |
| 5,214,308 | 5/1993 | Nishiguchi et al. | 257/692 |
| 5,217,922 | 6/1993 | Akasaki et al. | 437/183 |
| 5,325,265 | 6/1994 | Turlik et al. | 361/702 |
| 5,346,118 | 9/1994 | Degani et al. | 228/18.22 |
| 5,349,500 | 9/1994 | Casson et al. | 361/749 |
| 5,372,295 | 12/1994 | Abe et al. | 228/123.1 |
| 5,373,984 | 12/1994 | Wentworth | 228/180.1 |
| 5,387,551 | 2/1995 | Mizoguchi et al. | 437/209 |
| 5,393,696 | 2/1995 | Koh et al. | 437/183 |
| 5,488,014 | 1/1996 | Harada et al. | 437/192 |

*Primary Examiner*—Samuel M. Heinrich

[57] ABSTRACT

A method of thin film patterning by reflow. A first metal trace is deposited onto a surface of a substrate in a predetermined pattern. A second metal trace is then deposited onto the deposited first metal trace. Next, a thin film of a third metal is deposited onto the entire surface of the substrate and onto the deposited first and second metal traces. The substrate and the associated deposited metals are then heated to cause the deposited thin film of the third metal to flow and bead onto the second metal trace.

17 Claims, 3 Drawing Sheets

METHOD OF THIN FILM PATTERNING BY REFLOW

BACKGROUND OF THE INVENTION

1. Field of the Invention

This invention relates generally to patterning thin metal films onto a substrate. More particularly, this invention relates to the use of reflow techniques to redistribute thin films deposited over entire substrates.

2. Discussion

Thin metal films often must be patterned photolithographically using traditional etching or lift-off methods. Such is particularly the case in the fabrication of microelectronics. In the photolithographic patterning process, the film adheres to the substrate in selected areas, leaving other areas blank. A bonding/removal process enables the fabrication of connections where desired and also enables isolating conducting strips or traces where appropriate. Traditional approaches to thin film patterning often prove unsuitable because some metal layers are too thick for lift-off (or removal), while other metal layers are particularly susceptible to contamination from chemicals used during the photolithography process.

For example, when laser diode die bonding or wafer level packaging, indium films have many desirable characteristics, but are often several micrometers thick. These indium films typically oxidize fairly easily, which diminishes the bonding capability of the indium. Further, when indium films are used in wafer level packaging, photolithographic processes increase the likelihood that the indium will oxidize and/or become contaminated. These potentially contaminating processes include baking, rinsing, etching, and the like.

In another type of fabrication process, indium films are patterned by evaporation onto a substrate through shadow masks. The shadow masks have holes in selected areas of the mask in order to cast a shadow onto the substrate where the indium is desirably deposited. While the use of shadow masks significantly decreases the likelihood of contaminating the indium, the shadow mask process introduces several difficulties. First, shadow masks are often difficult to align with the substrate. Second, shadow masks cannot be used with closed curves, such as a circular trace, because the area outlining the closed trace must be attached to the remaining portion of the mask. For example, traditional fabrication techniques of integrated circuits often requires fabricating the electronic devices by fabricating multiples of the device on a silicon wafer, subdividing the electronic wafer into the individual devices, then packaging the electronic device.

In addition, the packaging portion of the integrated circuit process may optionally include hermetically sealing the device to further protect it within its packaging. Newer fabrication techniques desirably fabricate and package (or seal) the integrated circuit devices formed on the wafer before subdividing the wafer. This fabrication process is referred to as wafer level packaging. One method of wafer level packaging is described in U.S. patent application Ser. No. 08/009,530, entitled Mass Simultaneous Sealing and Electrical Connection of Electronic Devices, assigned to the assignee of the present invention and herein incorporated by reference. The above-referenced patent, however, does not exhaustively address the above-described issues of depositing the bonding material (the indium) while minimizing contamination in order to improve the quality of the hermetic sealing.

Therefore, it is desirable to provide a method and apparatus for patterning thin films while minimizing contamination and facilitating placement of the thin films on the substrate to effect suitable alignment of the thin film patterns.

SUMMARY OF THE INVENTION

This invention is directed to a method of thin film patterning by reflow. A first metal trace is deposited onto a surface of a substrate in a predetermined-pattern. A second metal trace is then deposited onto the deposited first metal trace. Next, a thin film of a third metal is deposited onto the entire surface of the substrate and onto the deposited first and second metal traces. The substrate and the associated deposited metals are then heated to cause the deposited thin film of the third metal to flow and bead onto the second metal trace.

Additional objects, advantages, and features of the present invention will become apparent from the following description and appended claims taken in conjunction with the accompanying drawings.

DETAILED DESCRIPTION OF THE DRAWINGS

Figure 1A:
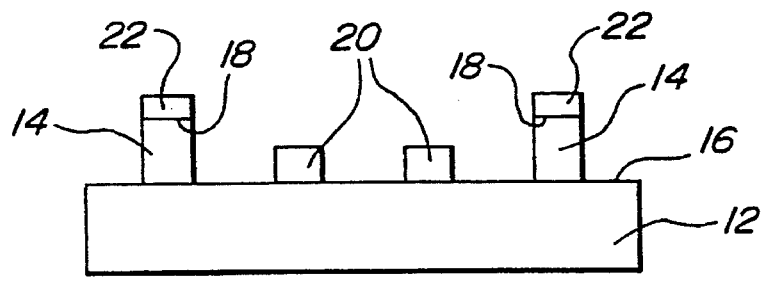
FIGS. 1a–c depict a cross-sectional view of a substrate and associated traces formed using the process according to the principals of the present invention.
Figure 1B:
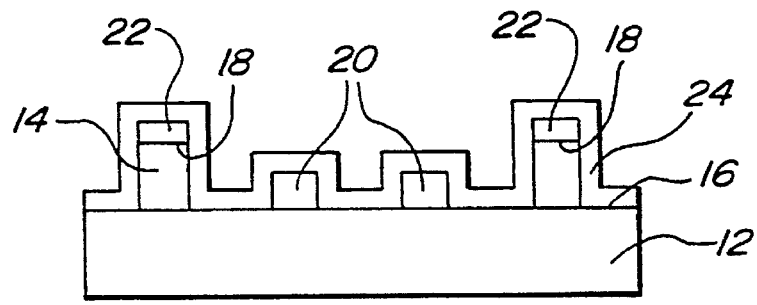

Referring to FIGS. 1a–c and 2, a silicon substrate and traces deposited thereon will be used to demonstrate the principals of the present invention. FIG. 1a depicts a silicon substrate 12 ($SiO_2$) on which is deposited copper traces 14 (as shown at block 15 of FIG. 2) using any of a number of known deposition processes. Examples of such deposition processes include thin and/or thick film deposition, electroless, and/or electro-plating. An adhesive metal film layer may optionally be applied between copper traces 14 and the substrate 12 to improve the copper to substrate bond. Copper traces 14 may, for example, form a grid of solder strips about the upper surface 16 of silicon wafer 12 or may form other selected patterns in accordance with the desired application, as is known in the art. A thin, inert metal layer, such as nickel, may then be deposited onto the top of copper traces 14 to prevent the copper from reacting with other metals to be applied thereto. A gold film is then patterned onto selected areas of surface 16 of silicon wafer 12 to form gold traces 20 and also onto the top surface 18 of copper traces 14 to form gold traces 22 (as shown at block 17 of FIG. 2). Gold traces 20 and 22 are deposited using electroplating or vacuum deposition processes. A layer of indium 24 is then evaporated onto the entire top surface 16 of substrate 12 (as shown at block 19 of FIG. 2) to yield the structure shown in FIG. 1b. It will be recognized by someone skilled in the art that metals other than indium such as lead, tin, or any alloy of these metals may readily be substituted for pure indium.

Figure 1C:
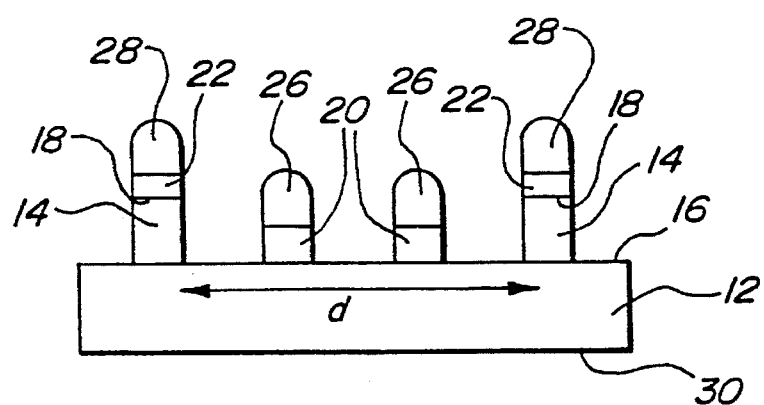
Figure 2:
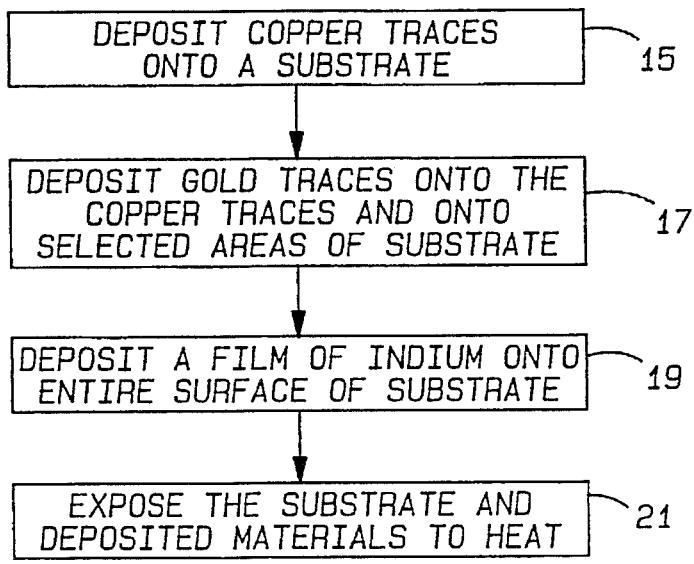
FIG. 2 is a flow diagram of the process for producing the apparatus of FIG. 1.

After the indium layer 24 is deposited onto the surface of silicon substrate 12, the entire structure is then heated, as shown at block 21 of FIG. 2, in a controlled atmosphere until the indium film changes to a liquid state. As the indium changes to a liquid state, it flows to gold traces 20 and 22 due to surface tension. This leaves those areas not initially covered by gold traces 20 and 22 substantially void of any indium and causes the indium to pool into beads or traces 26 and 28, covering gold traces 20 and 22, respectively, as shown in FIG. 1c.

Still referring to FIG. 1c, in areas where no indium is required, the gold traces 20, also referred to as getters, are deposited specifically to collect excess indium. This enables manufacturers to cover the entire surface with a layer of indium 24, rather than depositing the indium in specified locations, thereby facilitating the indium depositing progress. For example, assuming that no gold traces 20 were positioned between copper traces 14, the distance d between copper traces 14 may exceed the maximum distance over which the indium may flow during the reflow operation. Thus, the indium may not completely flow to gold traces 22, leaving excess deposits of indium between copper traces 14 at random locations upon the surface 16 of substrate 12. The excess deposits could cause shorts across electrically conductive components (not shown) located on the surface 16 of silicon substrate 12. Therefore, gold getters 20 are positioned between copper traces 14 where the distance d exceeds the flow distance of the indium during reflow. During reflow, the indium flows into beads 26 on top of getters 20, leaving top surface 16 of wafer 12 free of indium other than where desired.

Preferably, the getters 20 are positioned to minimize the possibility of shorts or other harmful effects to components mounted on substrate 12. Further, some applications require that the height of indium beads 28 exceeds the height of the gettered indium 26. For example, where a second wafer similar to wafer 12 has gold traces deposited on a surface as shown in FIG. 1c and the two wafers are to be bonded between their top surfaces, contact between the two wafers may desirably be limited to certain predetermined locations. Increasing the height of selected indium beads enables such selective bonding. Applying additional metal where appropriate to increase the bead height to a height higher than the gettered indium 26 may be accomplished using thick metal patterning, including electroplated copper processes.

With respect to heating the indium in order to initiate the reflow operation, a controlled atmosphere, such as hydrogen or forming gas ($H_2 + N_2$), suppresses oxidation until the indium film 24 changes state to a liquid and begins to flow. The indium changes state to a liquid and begins to flow at approximately 156 degrees Centigrade (C.). For example, the above-described controlled heating atmosphere typically operates in the temperature range of 180 degrees C. to 250 degrees C.

Figure 5:
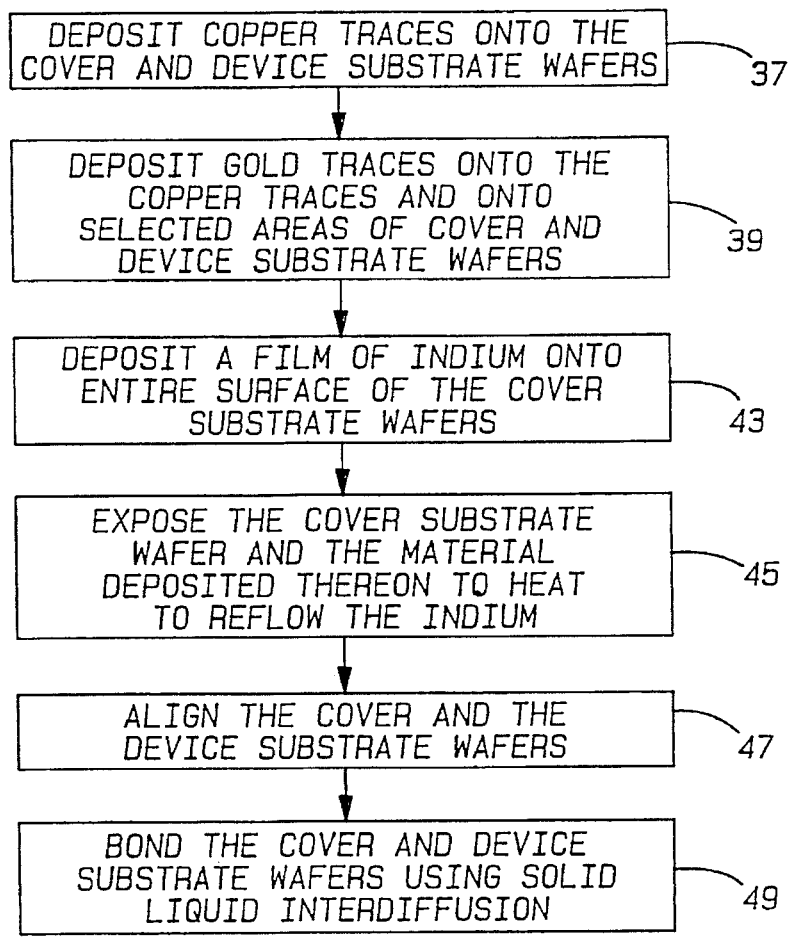
FIG. 5 is a flow diagram of the process for bonding the wafers depicted in FIG. 3 to effect a hermetic seal.
Figure 3:
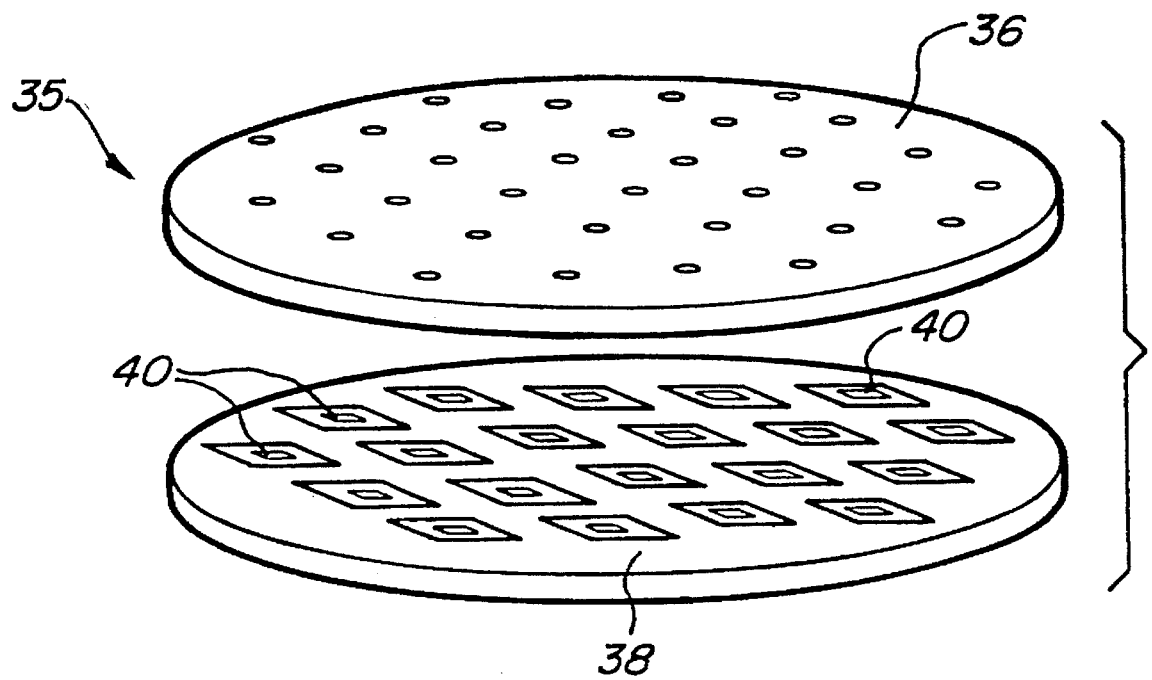
FIG. 3 depicts wafer to wafer bonding according to the principles of the present invention.
Figure 4:
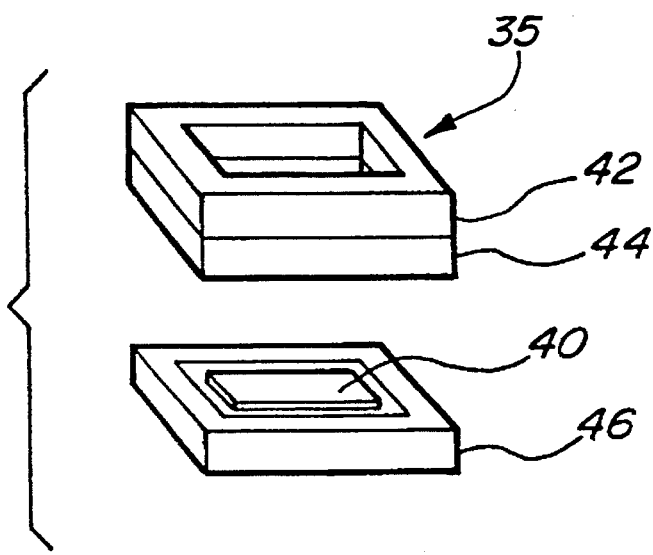
FIG. 4 depicts an enlarged view of a portion of the wafers shown in FIG. 3 in order to further demonstrate hermetically sealing electronic devices.

Referring to FIGS. 3–5, a particular application of the above-described indium reflow process will be described. By way of introduction, many electronic devices are sensitive and must be protected from harsh externalities, including various potentially damaging contaminants present in the environment. Hermetic packages have proven to be a very effective means for providing such protection. U.S. patent application Ser. No. 08/009,530 entitled Mass Simultaneous Sealing and Electrical Connection of Electronic Devices, which is referenced above, describes a method and apparatus for simultaneously manufacturing and hermetically sealing multiple electronic devices. This invention is particularly applicable to simultaneously, hermetically sealing such electronic devices.

Referring to FIG. 3, a cover substrate wafer 36 is shown aligned with device substrate wafer 38 to form assembly 35. Cover substrate 36 may optionally be an alumina substrate similar to silicon substrate 12 depicted in FIGS. 1a–c. Typically, each of the substrate wafers 36 and 38 are three inches in diameter, though they may be larger or smaller depending upon the particular application. Device substrate wafer 38 supports, as an example, a plurality of surface acoustic wave (SAW) transducers 40. The cover substrate wafer 36 is provided with a plurality of hermetically conductive holes 41 arranged to correspond in a predetermined manner with each of the SAW device terminals (not shown) on the device substrate wafer 38. To be described further herein, the wafers 36 and 38 are preferably aligned so that the contacts (not shown) of each SAW device 40 are aligned with the hermetic, conductive holes 41 of cover substrate 36.

To package the SAW device, cover substrate wafer 36 is bonded to device substrate wafer 38 as will be described. Preferably the bond is formed between corresponding grids of solder traces or strips. Referring particularly to FIG. 4, a copper trace (not shown) is first deposited onto cover substrate 36 and device substrate 38, as shown in block 37 of FIG. 5. Next, gold traces 42 and gold traces 46 are deposited onto the copper traces cover wafer substrate 36 and device substrate 38, respectively, and onto selected areas to act as getters (not shown) see block 39 of FIG. 5. A layer of indium is then deposited onto the surface of cover substrate 36, and the device is then heated to initiate reflow onto gold traces 42, as shown at block 43 and 45 of FIG. 5. The result is that gold traces 42 have fabricated thereon indium beads 44.

Gold traces 46 of device substrate wafer 38 form a border around electronic devices 40 and are patterned to substantially correspond to indium traces 44 so that the indium traces 44 and gold 46 correspond to effect a suitable bond. The device substrate wafer 38 and cover substrate wafer 36 are then aligned for bonding, as shown at block 47 of FIG. 5. Gold traces 46 and indium traces 44 are preferably bonded through a hermetic solid liquid interdiffusion (SLID) bond formed between the two layers, as shown at block 49 of FIG. 5. Such a bond provides a hermetic seal between cover substrate wafer 36 and device substrate wafer 38 to suitably seal device 40. Further, to achieve a hermetic seal, it is important to insure that conductive holes 41 of cover substrate wafer 36 are hermetically sealed as well, which enables electronic interconnection with the device 40. Note that an alternative and simpler bonding method omits the initial reflow step after depositing the indium and immediately aligns the device with the substrate. In this manner, the bonding and indium reflow processes, shown at blocks 45 and 49, can be performed simultaneously.

With regard to the process described in FIGS. 3–5, bonding between cover substrate wafer 36 and device substrate wafer 38 requires a relatively low temperature (in the range of 170 degrees C. to 230 degrees C.) to minimize potential thermal stresses incurred upon cooling due to mismatched thermal expansion characteristics between the two wafers. Further, the bond must have a high melting temperature (in the range of 200 degrees C. to 260 degrees C.) so that once formed, the bond will not subsequently melt in later assembly processes, such as surface mount processes on a circuit board.

Bonding between the gold traces 46 and indium traces 44 substantially accomplishes these desired bond characteristics goals. First, gold traces 42 and 46 are formed directly upon the cover substrate wafer 36, and the indium traces 44 are formed directly upon the gold traces 42, both of which lie on cover substrate wafer 36. When the two substrate wafers 36 and 38 are aligned, placed in an atmosphere of dry gas (e.g., hydrogen or nitrogen or vacuum), and heated, the indium 44 melts at 155 degrees Celsius and begins to mix with the gold. At a sufficient gold concentration, the melt passes through a phase transition and becomes solid. By using a suitable ratio of gold and indium (e.g., 30 to 80 percent weight of indium), after the solid has annealed, the bond will not melt below 400 degrees. This bond melting temperature is considerably higher than a typical printed circuit board soldering temperature which is typically less than 250 degrees Celsius. In addition, getters 20 depicted in FIG. 1 may optionally be used on cover substrate wafer 36 within the interior of the combined gold layer 42 and indium layer 44 in order to prevent excess indium from forming on unwanted portions of cover substrate wafer 36.

It is to be understood that the foregoing description is primarily intended to be exemplary, in particular to provide the preferred embodiments of the invention as contemplated by the inventors. The foregoing description is not meant to be limiting. Accordingly, various changes and modifications may be made without departing from the spirit and scope of the invention as defined by the appended claims.

We claim:

1. A method of thin film patterning, comprising the steps of:

depositing a first metal trace onto a surface of a substrate in a predetermined pattern;

depositing a second metal trace onto the deposited first metal trace;

depositing a thin film of a third metal onto the entire surface of the substrate and onto the deposited first and second metal traces; and heating the substrate and associated deposited metals to cause the deposited thin film of the third metal to flow and bead onto the second metal trace.

2. The method as defined in claim 1 further comprising the step of depositing the second metal onto preselected areas of the substrate to define collection spots for collecting excess amounts of the third metal.

3. The method as defined in claim 2 wherein the first metal is copper.

4. The method as defined in claim 3 wherein the second metal is gold.

5. The method as defined in claim 4 wherein the third metal is indium.

6. A method of bonding two substrates, comprising the steps of:

depositing a trace of a first metal in a predetermined pattern onto a surface of a first substrate;

depositing a trace of the first metal in substantially the same predetermined pattern onto a surface of a second substrate;

depositing a film of a second metal onto the surface of the first substrate;

heating the first substrate and associated deposited metals to cause the deposited thin film of the second metal to flow and bead onto the first metal trace;

aligning the surface of the first substrate with the surface of the second substrates in accordance with the predetermined patterns;

initiating a bond between the second metal of the first substrate and the first metal of the second substrate to bond the first and second substrates.

7. The method as defined in claim 6 further comprising the step of depositing the first metal onto preselected areas of the first substrate to define collection spots for collecting excess amounts of the second metal.

8. The method as defined in claim 7 further comprising the step of initially depositing a third metal onto the first substrate, the first metal being applied to the third metal.

9. The method as defined in claim 8 further comprising the step of initially depositing a third metal onto the second substrate, the first metal being applied to the third metal.

10. The method as defined in claim 9 further comprising the step of depositing the first metal onto preselected areas of the first substrate to define collection spots for collecting excess amounts of the second metal.

11. The method as defined in claim 10 wherein the step of initiating a bond between the first and second metal is effected using a solid liquid interdifusion process.

12. The method as defined in claim 11 further comprises the step of fabricating an electronic device on one of the first or second substrates and patterning the first metal to define a border around the integrated circuit.

13. The method as defined in claim 12 wherein the step of initiating a bond between the first and second metals effects a hermetic seal of the integrated circuit.

14. The method as defined in claim 10 wherein the first metal is gold.

15. The method as defined in claim 10 wherein the second metal is indium.

16. The method as defined in claim 10 wherein the third metal is copper.

17. The method as defined in claim 6 wherein the steps of heating the first substrate and initiating a bond between the metal layers are combined.

* * * * *